US00PP30802P2

(12) United States Plant Patent
Bron et al.

(10) Patent No.: US PP30,802 P2
(45) Date of Patent: Aug. 13, 2019

(54) ***MISCANTHUS* PLANT NAMED 'EMPMIS01'**

(50) Latin Name: *Miscanthus sinensis*
Varietal Denomination: EMPMIS01

(71) Applicants: Hogendoorn Holland B.V., Wijk en Aalburg (NL); Empho B.V., Beritsum (NL)

(72) Inventors: Piet Bron, Beritsum (NL); Elbert van Vulpen, Wijk en Aalburg (NL)

(73) Assignee: PIRO NEW PLANTS, Sloten (NL)

( * ) Notice: Subject to any disclaimer, the term of this patent is extended or adjusted under 35 U.S.C. 154(b) by 0 days.

(21) Appl. No.: 15/732,708

(22) Filed: Dec. 18, 2017

(51) Int. Cl.
*A01H 5/12* (2018.01)

(52) U.S. Cl.
USPC ..... Plt./384

(58) Field of Classification Search
USPC ..... Plt./384
CPC ..... A01H 5/12
See application file for complete search history.

*Primary Examiner* — Keith O. Robinson
(74) *Attorney, Agent, or Firm* — Penny J. Aguirre

(57) ABSTRACT

A new cultivar of *Miscanthus, Miscanthus sinensis* 'EMPMIS01', that is characterized by its flower plumes that are dark red in color, its compact plant habit and short plant height, its long flowering period, and its floriferous blooming habit in producing numerous flowering stems.

2 Drawing Sheets

Botanical classification: *Miscanthus sinensis.*
Cultivar designation: 'EMPMIS01'.

CROSS REFERENCE TO A RELATED APPLICATION

This application is related to a European plant breeders' rights application filed on Apr. 20, 2015, application No. 2015/0874. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Miscanthus sinensis* and will be referred to hereafter by its cultivar name, 'EMPMIS01'. 'EMPMIS01' represents a new cultivar of Japanese silver grass, a cold hardy, perennial ornamental grass grown for landscape use.

'EMPMIS01' was discovered by the Inventors as a chance seedling in a trial field in Berltsum, The Netherlands in August of 2010. The parentage is unknown.

Asexual propagation of the new cultivar was first accomplished by division by one of the Inventors in Harich, The Netherlands in January 2015. Asexual propagation by division has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'EMPMIS01' as a unique cultivar of *Miscanthus.*

1. 'EMPMIS01' exhibits flower plumes that are dark red in color.

2. 'EMPMIS01' exhibits a compact plant habit and short plant height.
3. 'EMPMIS01' exhibits a long flowering period.
4. 'EMPMIS01' exhibits a floriferous blooming habit in producing numerous flowering stems.

'EMPMIS01' can be most closely compared to the cultivar 'Kleine Fontaine' (not patented) and 'Gracillimus' (not patented). 'Kleine Fontaine' is similar to 'EMPMIS01' in having weeping inflorescences. 'Kleine Fontaine' differs from 'EMPMIS01' in having a taller plant height, flowers that are light red in color, and a shorter blooming period. 'Gracillimus' is similar to 'EMPMIS01' in having coppery red flowers when opening and thin foliage with a white midrib. 'Gracillimus' differs from 'EMPMIS01' in having a taller plant height and in blooming later in the season.

BRIEF DESCRIPTION OF THE DRAWINGS

The accompanying colored photographs illustrate the overall appearance and distinct characteristics of the new *Miscanthus*. The photographs were taken in September of plants 4 years in age as grown outdoors in a 40-cm container in Berltsum, The Netherlands.

The photograph in FIG. 1. provides a side view of a plant of 'EMPMIS01' and illustrates the overall plant habit and general appearance in bloom.

Figure 1:
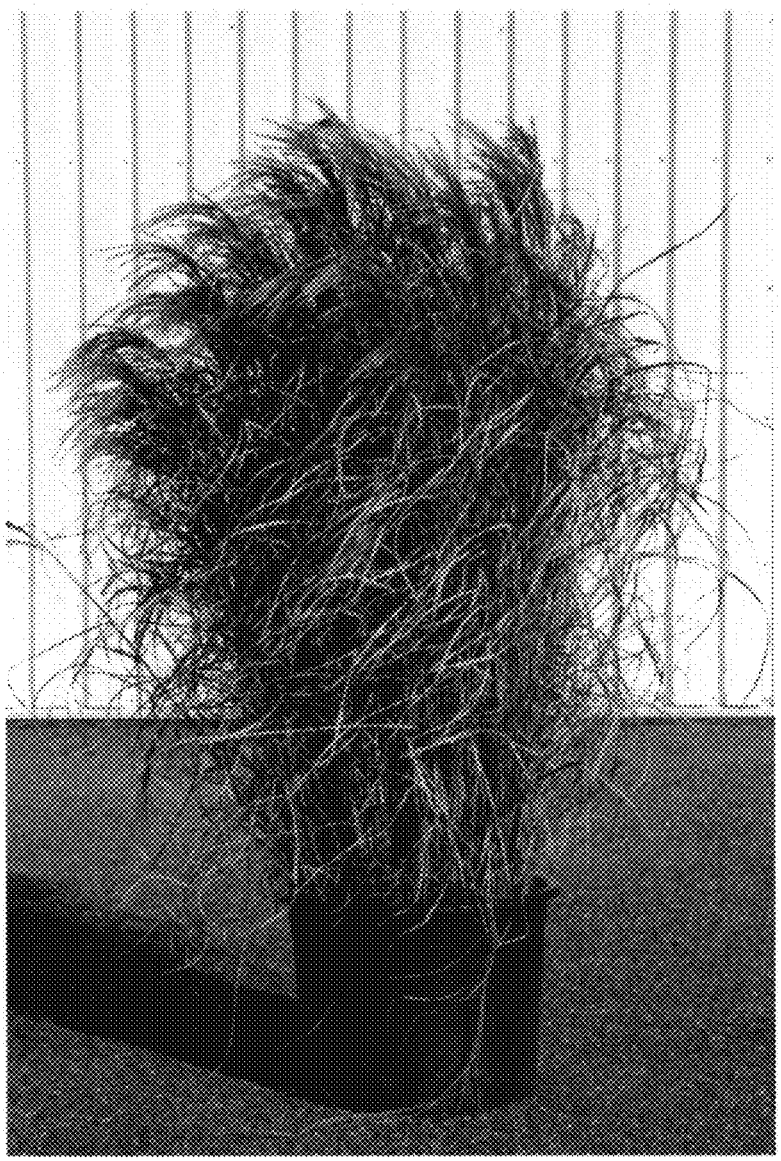
Figure 2:
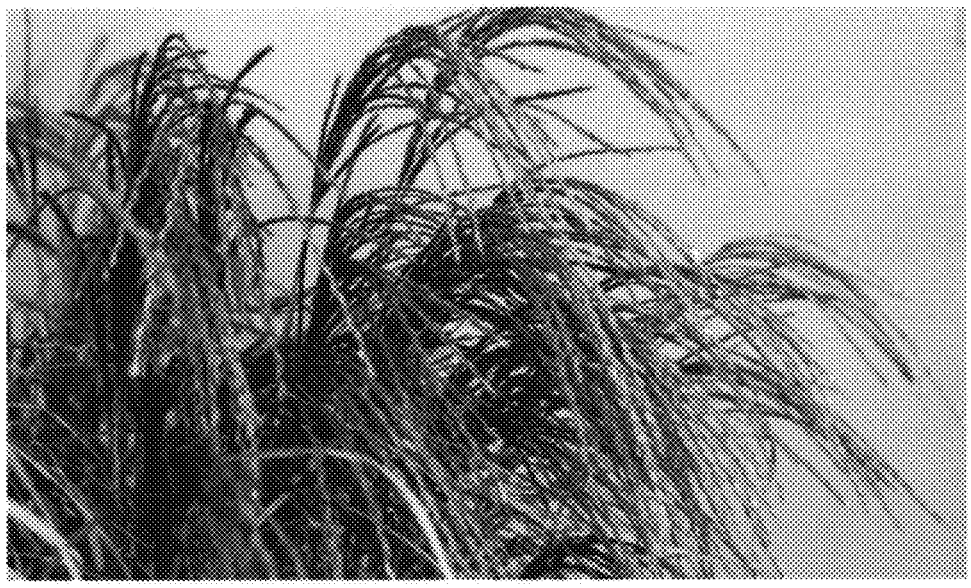

The photograph in FIG. 2. provides a close-up view of the inflorescences of 'EMPMIS01.

Figure 3:
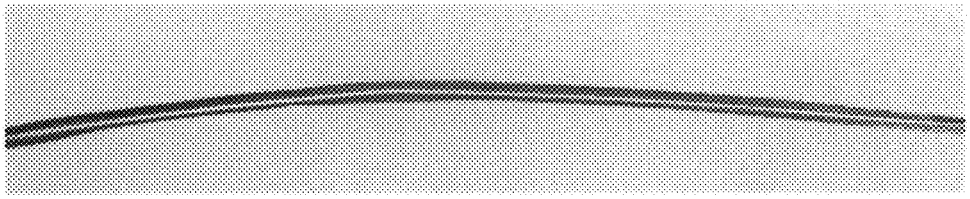

The photograph in FIG. 3. provides a close-up view of a leaf of 'EMPMIS01'.

The colors in the photographs are as close as possible with the photographic and printing technology utilized and the color values cited in the Detailed Botanical Description accurately describe the colors of the new *Miscanthus.*

DETAILED BOTANICAL DESCRIPTION

The following is a detailed description of 4 year-old plants of the new cultivar as grown outdoors in September in 40-cm containers Berltsum, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Blooms in July through September in The Netherlands.

*Plant type.*—Herbaceous perennial.

*Plant habit.*—Clump-forming, ornamental grass with an upright, broad form and dense, compact bushy foliage.

*Height and spread.*—Average of 1.1 m in height (from soil to top of foliar plane), 1.28 m in height (from soil to top of floral plane), 1.31 m in diameter.

*Hardiness.*—At least in U.S.D.A. Zones 6 to 10.

*Diseases and pests.*—No susceptibility or resistance to diseases or pests has been observed.

*Root description.*—Fibrous.

*Root development.*—An average of 4 months for root initiation and an average of 6 months to produce a young rooted plant.

*Propagation.*—Semi-hardwood stem cuttings and division.

*Growth rate.*—Moderately vigorous.

Stem description:

*General.*—Rounded, strong.

*Stem aspect.*—Growing from the base, held upright, vertically.

*Stem quantity.*—Average of 250 basal shoots.

*Stem color.*—Young 150C, mature N144A, internodes 156C, tinged with 175B.

*Stem size.*—An average of 90.5 cm in length (from base of shoots to base of inflorescence), 3 mm in diameter, internode 6.8 cm in length.

*Stem surface.*—Moderately glossy.

*Stem nodes.*—An average of 4 mm in diameter, N144A and tinged 175B in color, glabrous surface.

Foliage description:

*Leaf shape.*—Linear.

*Leaf division.*—Simple.

*Leaf base.*—Sheathed.

*Leaf apex.*—Narrow and long acuminate.

*Leaf aspect.*—Slightly carinate, tips twisted, leaves arching.

*Leaf venation.*—Parallel, only main vein is visible, upper surface color N155A, lower surface color 138B.

*Leaf margins.*—Entire, with sharp short bristles that are not visually noticeable.

*Internode length.*—An average of 6.8 cm.

*Leaf size.*—An average of 48.1 cm in length, an average of 5 mm in width, sheath length 15.7 cm, sheath width 5 mm.

*Leaf surface.*—Upper and lower surface glabrous and smooth, matte, ligules; moderately pubescent with thin hairs an average of 2 mm in length and NN155A in color.

*Leaf number.*—An average of 12 per shoot.

*Leaf arrangement.*—Alternate.

*Leaf color.*—Young upper surface; 143A, young lower surface 138A, mature upper surface between 143A and 146A, mature lower surface 146B to 146C.

Flower description:

*General description.*—Compact, fan-shaped panicle terminating from each stem, composed of numerous slender, silky aggregate racemes, cascadin, spikelets arranged in pairs on individual zig-zag like racemes.

*Lastingness of inflorescence.*—Average of 1 month, persistent.

*Fragrance.*—None.

*Panicle size.*—An average of 18.7 cm in length and 16 cm in width.

*Panicle color.*—A blend of 164A and 164B.

*Flower number.*—430 flowers per inflorescence, average of 50,000 flowers per plant.

*Flower buds.*—An average of 7 mm in length, 2 mm in diameter, narrow ovate in shape, 161A to 161B in color, surface is smooth, glabrous, moderately glossy and covered with fine hairs extending from the base of the floret.

*Flowers.*—Single, consisting of two glumes, one palea and one lemma, upright aspect, freely flowering habit, average of 2 mm in height and diameter, 8 mm in depth.

*Peduncle.*—An average of 17.9 cm in length and 0.6 mm in width, moderately strong, smooth and glabrous, moderately glossy and 144B in color.

*Pedicels.*—An average of 4 mm in length and 0.4 mm in width, moderately strong, smooth and glabrous, moderately glossy and 144B in color.

*Spikelet description.*—Consisting of 2 glumes, 1 palea, 1 lemma, surface slightly glossy, ovate in shape, strongly concave, base cuneate, no venation visible, not fading, 2 glumes oppositely placed at the base of each individual flower, lemma and palea oppositely placed above the glumes, margins of glumes and lemma entire, margins of palea fringed, apex of glumes and palea acute, apex of lemma narrow acute, average length of lower glume 4.5 mm, upper glume 6 mm in length, length of lemma 8 mm, length of palea 4 mm, glume and palea width 0.75 mm, width of lemma 0.5 mm, color; when opening both sides of glumes 164C, lemma and palea N155A, tip of lemma 165B, one whorl of fine hairs extending from the base of the floret; average of 1 cm in length, 156D and tinged 181C in color, overall flower color; a blend of 164A, 164B, 164C and 165B.

Reproductive organs:

*Androecium.*—Stamens; average of 2, anthers; narrow oblong in shape, 1.5 mm in length, 0.3 mm in width, 166B in color, filament; average of 2 mm in length, transparent and NN155D, pollen; none.

*Gynoecium.*—Pistil; 2, 3 mm in length, stigmas; feather-like, 2 mm in length, 0.1 mm in diameter, 200A in color, style; 1 mm in length, NN155D in color, ovary; 144A to 144B in color.

*Caryopsis.*—No caryopsis production was observed.

It is claimed:

1. A new and distinct cultivar of *Miscanthus* plant named 'EMPMIS01' as herein illustrated and described.

* * * * *